(12) United States Patent
Skiba

(10) Patent No.: US 7,457,667 B2
(45) Date of Patent: Nov. 25, 2008

(54) CURRENT PRODUCING SURFACE FOR A WOUND DRESSING

(75) Inventor: Jeffry B Skiba, Oracle, AZ (US)

(73) Assignee: Silverleaf Medical Products, Inc., Scottsdale, AZ (US)

( * ) Notice: Subject to any disclaimer, the term of this patent is extended or adjusted under 35 U.S.C. 154(b) by 692 days.

(21) Appl. No.: 10/784,088

(22) Filed: Feb. 19, 2004

(65) Prior Publication Data

US 2005/0187580 A1  Aug. 25, 2005

(51) Int. Cl.
*A61N 1/04*  (2006.01)
*A61N 1/24*  (2006.01)
*A61M 35/00*  (2006.01)

(52) U.S. Cl. .......................... 607/50; 607/152; 604/20; 600/372; 600/391

(58) Field of Classification Search .................. 607/115, 607/152, 1–2, 98–99, 108–112, 139–149, 607/50; 604/20, 46, 500, 290; 606/34; 602/41; 600/372, 382–393, 395–397; 427/2.1, 2.31; 156/277, 278, 260; 264/129–132; 118/46

See application file for complete search history.

(56) References Cited

U.S. PATENT DOCUMENTS

| | | | |
|---|---|---|---|
| 116,562 A | 7/1871 | Collins | |
| 167,162 A | 8/1875 | French | |
| 175,974 A | 4/1876 | Hall | |
| 222,276 A | 12/1879 | Hunter | |
| 393,741 A | 12/1888 | Collins | |
| 3,774,592 A * | 11/1973 | Lahr | .......................... 600/392 |
| 3,848,608 A * | 11/1974 | Leonard | ....................... 607/63 |
| 4,034,750 A | 7/1977 | Seiderman | |
| 4,067,342 A * | 1/1978 | Burton | ........................ 607/152 |
| 4,142,521 A | 3/1979 | Konikoff | |
| 4,211,222 A * | 7/1980 | Tapper | .......................... 604/20 |
| 4,528,265 A | 7/1985 | Becker | |
| 4,529,623 A | 7/1985 | Maggs | |
| 4,540,604 A * | 9/1985 | Siuta | .......................... 427/97.4 |
| 4,569,673 A | 2/1986 | Tesi | |
| 4,585,652 A | 4/1986 | Miller et al. | |
| 4,657,808 A | 4/1987 | Maggs | |
| 4,767,401 A | 8/1988 | Seiderman | |

(Continued)

FOREIGN PATENT DOCUMENTS

GB   1588933   4/1981

(Continued)

OTHER PUBLICATIONS

"A powerful combination for the care of chronic wounds", http://www.jnjgateway.com/home.jhtml?loc=USENG&page=viewContent&contentId=090 . . . , (Observed Jan. 13, 2005),2 pages.

(Continued)

*Primary Examiner*—Kennedy J. Schaetzle
*Assistant Examiner*—Jessica Reidel
(74) *Attorney, Agent, or Firm*—Lowell W. Gresham; Jordan M. Meschkow; Charlene R. Jacobsen

(57) ABSTRACT

In an embodiment, an article includes a primary surface, and a pattern of spaced dissimilar materials, on the primary surface. The pattern is to spontaneously produce electrical surface currents when brought into contact with an electrically conducting solution.

7 Claims, 2 Drawing Sheets

U.S. PATENT DOCUMENTS

| | | | |
|---|---|---|---|
| 4,817,594 A | | 4/1989 | Juhasz |
| 4,852,571 A | * | 8/1989 | Gadsby et al. ............... 600/396 |
| 4,937,323 A | | 6/1990 | Silver et al. |
| 5,053,001 A | | 10/1991 | Reiler et al. |
| 5,143,079 A | * | 9/1992 | Frei et al. .................... 600/547 |
| 5,288,289 A | | 2/1994 | Haak et al. |
| 5,298,017 A | | 3/1994 | Theeuwes et al. |
| 5,322,520 A | | 6/1994 | Milder |
| 5,352,315 A | * | 10/1994 | Carrier et al. ................ 156/267 |
| 5,360,440 A | | 11/1994 | Andersen |
| 5,405,317 A | | 4/1995 | Myers et al. |
| 5,454,886 A | | 10/1995 | Burrell et al. |
| 5,681,575 A | | 10/1997 | Burrell et al. |
| 5,685,837 A | | 11/1997 | Horstmann |
| 5,695,857 A | | 12/1997 | Burrell et al. |
| 5,725,817 A | | 3/1998 | Milder |
| 5,741,224 A | | 4/1998 | Milder et al. |
| 5,753,251 A | | 5/1998 | Burrell et al. |
| 5,759,564 A | | 6/1998 | Milder et al. |
| 5,770,255 A | | 6/1998 | Burrell et al. |
| 5,772,688 A | * | 6/1998 | Muroki .......................... 607/1 |
| 5,782,788 A | | 7/1998 | Widemire |
| 5,814,094 A | | 9/1998 | Becker et al. |
| 5,837,275 A | | 11/1998 | Burrell et al. |
| 5,944,685 A | | 8/1999 | Muroki |
| 5,958,440 A | | 9/1999 | Burrell et al. |
| 5,974,344 A | * | 10/1999 | Shoemaker, II ............. 607/149 |
| 5,985,308 A | | 11/1999 | Burrell et al. |
| 6,017,553 A | | 1/2000 | Burrell et al. |
| 6,038,485 A | * | 3/2000 | Axelgaard ................... 607/148 |
| 6,080,490 A | | 6/2000 | Burrell et al. |
| 6,087,549 A | | 7/2000 | Flick |
| 6,181,963 B1 | | 1/2001 | Chin et al. |
| 6,238,686 B1 | | 5/2001 | Burrell et al. |
| 6,248,449 B1 | * | 6/2001 | Watanabe .................... 428/458 |
| 6,287,484 B1 | | 9/2001 | Hausslein et al. |
| 6,306,419 B1 | | 10/2001 | Vachon |
| 6,333,093 B1 | | 12/2001 | Burrell et al. |
| 6,365,220 B1 | | 4/2002 | Burrell et al. |
| 6,522,918 B1 | | 2/2003 | Crisp et al. |
| 6,582,713 B2 | | 6/2003 | Newell et al. |
| 6,631,294 B2 | | 10/2003 | Andino et al. |
| 6,723,350 B2 | | 4/2004 | Burrell et al. |
| 6,738,662 B1 | | 5/2004 | Frank |
| 6,788,978 B2 | | 9/2004 | Vesnaver |
| 6,861,570 B1 | | 3/2005 | Flick |
| 2002/0004640 A1 | * | 1/2002 | Conn et al. ................... 604/20 |
| 2002/0122787 A1 | | 9/2002 | Newell et al. |
| 2002/0161405 A1 | | 10/2002 | Druko |
| 2002/0182485 A1 | * | 12/2002 | Anderson et al. ........... 429/105 |
| 2002/0188282 A1 | | 12/2002 | Greenberg |
| 2003/0074042 A1 | * | 4/2003 | Gadsby et al. ............... 607/152 |
| 2003/0144723 A1 | | 7/2003 | Andino et al. |
| 2004/0015223 A1 | | 1/2004 | Andino et al. |
| 2004/0030276 A1 | | 2/2004 | Flick |
| 2004/0049145 A1 | | 3/2004 | Flick |
| 2004/0059282 A1 | | 3/2004 | Flock et al. |
| 2004/0162602 A1 | * | 8/2004 | Cohen ......................... 607/142 |
| 2004/0167461 A1 | | 8/2004 | Nitzan et al. |
| 2004/0193089 A1 | | 9/2004 | Fischer et al. |
| 2004/0199086 A1 | | 10/2004 | Crisp |
| 2004/0265395 A1 | | 12/2004 | Sun et al. |
| 2004/0267169 A1 | | 12/2004 | Sun et al. |
| 2004/0267231 A1 | | 12/2004 | Sun et al. |
| 2004/0267232 A1 | | 12/2004 | Sun et al. |
| 2004/0267237 A1 | | 12/2004 | Sun et al. |
| 2005/0004506 A1 | | 1/2005 | Gyory |
| 2005/0004508 A1 | | 1/2005 | Sun et al. |
| 2005/0004509 A1 | | 1/2005 | Sun et al. |
| 2005/0004550 A1 | | 1/2005 | Sun et al. |
| 2005/0010161 A1 | | 1/2005 | Sun et al. |
| 2005/0010192 A1 | | 1/2005 | Sun et al. |
| 2005/0015042 A1 | | 1/2005 | Sun et al. |
| 2005/0085751 A1 | | 4/2005 | Daskal et al. |
| 2005/0125006 A1 | | 6/2005 | Nady |
| 2005/0125009 A1 | | 6/2005 | Perry et al. |
| 2005/0125012 A1 | | 6/2005 | Houser et al. |
| 2005/0125016 A1 | | 6/2005 | Trerotola |
| 2005/0125018 A1 | | 6/2005 | Galloway et al. |
| 2005/0125021 A1 | | 6/2005 | Nance et al. |
| 2005/0148996 A1 | | 7/2005 | Sun et al. |
| 2005/0192636 A1 | | 9/2005 | Skiba et al. |
| 2006/0015052 A1 | * | 1/2006 | Crisp ............................ 602/41 |
| 2006/0015053 A1 | * | 1/2006 | Crisp ............................ 602/43 |

FOREIGN PATENT DOCUMENTS

| | | |
|---|---|---|
| JP | 03-080874 A2 | 4/1991 |
| WO | WO-0112157 A1 | 2/2001 |
| WO | WO-2004022033 A1 | 3/2004 |

OTHER PUBLICATIONS

"Managing chronic wounds", http://wound.smith-nephew.com/us/node.asp?NodeId=2871, (Observed Jan. 13, 2005),2 pages.

"Silver-Powered Antimicrobial Dressing", http://www.convatec.com/ag/us/index.html?ref=brandsite, (Observed Jan. 13, 2005),1 pages.

"International Search Report filed in corresponding PCT application No. PCT/US2005/005355", (Jun. 15, 2005), 8 pages.

* cited by examiner

CURRENT PRODUCING SURFACE FOR A WOUND DRESSING

BACKGROUND OF THE INVENTION

Bandages and wound dressings are simple, familiar devices. In an effort to hasten the wound healing process or reduce the risk of infection, there have been many recent efforts to redesign, or sometimes redefine, a bandage. Few people have enjoyed the benefits of some new bandages, because they are either too complex or too expensive.

The major advances in the art of wound healing are usually either improved methods for reducing infection or stimulating cell repair. It is now known that a moist wound heals faster and is less likely to scar than a dry wound, so the use of traditional bandages to keep a wound moist and protected is correct. It is also known that silver is an anti-microbial agent, so there are numerous products that deliver silver to a wound, such as Smith & Nephew$^{SM}$ ACTICOAT 7™, Johnson & Johnson® ACTISORB™, and Bristol-Meyers Squibb$^{SM}$ HYDROFIBER®.

Covering a wound is easy, and there are numerous products that fill that need. Delivering silver to a wound, however, has posed many difficulties because silver is a metal. Some methods resort to using silver crystals, which have a large relative surface area. Colloidal silver, silver salts (e.g. silver nitrate) and silver compounds (e.g. silver sulfadiazine) have been used to make creams and ointments. Creams and ointments are popular in the field of medicine because they are easy to use and familiar.

There are devices that rely on either an external electrical power source or a direct reaction between silver and another metal to generate the production of silver ions. One technology, described in U.S. Pat. Nos. 4,657,808 and 4,529,623 to Frederick Maggs consists of activated carbon with silver dispersed within it. Other technologies, described in U.S. Pat. Nos. 5,681,575, 5,753,251, 5,770,255, and 5,837,275 to Dr. Robert Burrell, et al., use vapor deposition techniques to apply a coating of silver onto a medical device. Yet another technology, described in U.S. Pat. No. 5,814,094 to Dr. Robert O. Becker, uses electricity (often from a coin battery) to produce free silver ions that may penetrate into the wound tissue. And yet another technology, described in U.S. Pat. No. 6,522,918 to Dr. William E. Crisp, et al., combines silver and another metal-bearing material within a thickness of material, such as a sponge. Unfortunately, these devices may require expensive manufacturing processes, and the devices themselves can be complex and cumbersome.

SUMMARY OF THE INVENTION

In an embodiment, an article includes a primary surface, and a pattern of spaced dissimilar materials, on the primary surface. The pattern is to spontaneously produce electrical surface currents when brought into contact with an electrically conducting solution.

Figure 1:
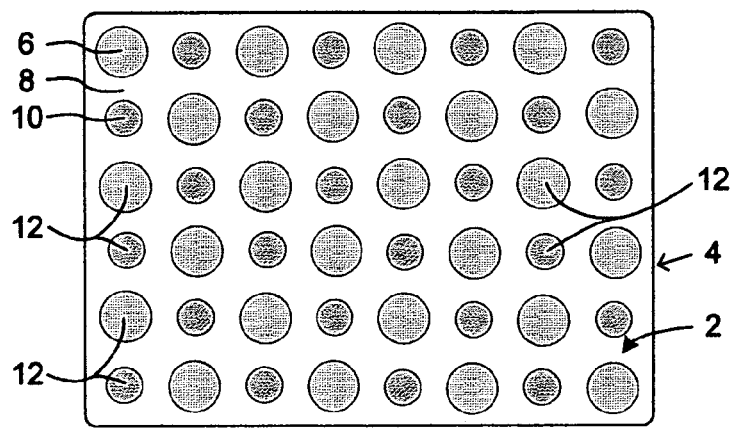
FIG. 1 is a detailed plan view of a very basic embodiment of the present invention.

The reference numbers used in the various Figs. are as follows:
2 primary surface
3 cross-section
4 article
6 first design
8 spacing
10 second design
12 repetition
14 pattern
16 elastic adhesive layer
18 overlapping piece
20 back of the printed dressing material
22 absorbent cloth layer
24 fine lines

DETAILED DESCRIPTION OF THE INVENTION

The detailed description of embodiments of the present invention has been broken into two sections. The first section will teach how to make preferred and alternate embodiments. The second section explores theories that may explain why embodiments of the present invention achieve beneficial results, but it is not necessary to understand these theories in order to make, use or otherwise benefit from embodiments of the present invention. Any inaccuracies or oversimplifications of the theories presented in the second section should in no way detract from the scope of the claims, which focus on the embodiments and not the theories.

A preferred embodiment includes a bandage, more generally a wound dressing, but a method for making a wound dressing, in accordance with an embodiment of the present invention, can similarly be applied to virtually any medical device that contacts an electrolyte of the body, as will be apparent to one of skill in the art, based on the description herein. Actually, embodiments of the present invention can be applied to virtually any non-conductive surface that may come into contact with an electrolytic solution. A purpose of using the present invention is to reduce infection and contamination, but there are additional benefits specific to wound care that are of exceptional value. These benefits will be addressed in the second section.

Over 200 years ago, in 1800, Alessandro Volta assembled the first modern battery. He sandwiched a saltwater-soaked piece of paper between a zinc disc and a silver disc, and was electrically shocked by the potential difference, or voltage, that was created by his assembly. Volta's electrochemical cell generated an electrical current because of a spontaneous oxidation-reduction reaction. In his honor, this type of electrochemical cell is called a voltaic cell, but may also be referred to as a galvanic cell. In the case of silver and zinc, electrons are transferred from zinc metal to silver ions. The oxidation half reaction of zinc metal results in the loss of two electrons to produce zinc ion, and the reduction half reaction of silver ion results in the gain of one electron to produce silver metal. The zinc electrode is the anode (negative sign) and the silver electrode is the cathode (positive sign), because the electrons flow from zinc to silver. The flow of ions generates the electrical current, so the silver and zinc cannot directly contact each other or there will be a direct reaction with no current generated. An electrolyte, such as table salt, dissolves in water to provide an electrically conducting solution which electrically bridges the gap between the two dissimilar metals so that there is a current flow caused by the spontaneous reactions between the physically separated metals.

Dissimilar metals used to make the preferred embodiment of the present invention (a wound dressing) are silver and zinc, and the electrolytic solution includes sodium chloride in water. A unique aspect of some embodiments of the present invention is that the electrodes are painted or printed onto a non-conductive surface to create a pattern, most preferably an array, of voltaic cells that do not spontaneously react until they contact an electrolytic solution, such as wound fluid. The remainder of this description will use the terms "printing" with "ink", but it is understood that the embodiments may instead be "painted" with "paints". It is also assumed that a competent printer will know how to properly apply and cure the inks without any assistance, other than perhaps instructions that should be included with the selected binder that is used to make the ink mixtures that will be used in the printing process.

In FIG. 1, the electrodes are printed onto a desired primary surface 2 of an article 4 which, in the preferred embodiment, is that surface of a wound dressing that comes into direct contact with a wound. In alternate embodiments of the present invention, the primary surface is one which simply should be antimicrobial, such as a medical instrument, implant, surgical gown, gloves, socks, table, door knob, or other surface that will contact an electrolytic solution, including sweat, so that at least part of the pattern of voltaic cells will spontaneously react and kill bacteria or other microbes.

The printed electrodes adhere or bond to the primary surface 2 because a biocompatible binder is mixed, into separate mixtures, with each of the dissimilar metals that will create the pattern of voltaic cells, in an embodiments. Most inks are simply a binder mixed with pigment. Similarly, the metal inks are a binder mixed with a conductive element. The resulting metal ink mixtures may be used with an application method, such as screen printing, in an embodiment, to apply the electrodes to the primary surface in predetermined patterns. Once the inks dry and/or cure, the patterns of spaced electrodes will substantially maintain their relative position, even on a flexible material such as cloth. To make only a few of the wound dressings of an embodiment of the present invention, the mixtures can be hand painted onto a common adhesive bandage so that there is an array of alternating electrodes that are spaced about a millimeter apart on the primary surface of the bandage. The paint should be allowed to dry before being applied to a wound so that the zinc ink does not mix with the silver ink, which would destroy the array and cause direct reactions that will release the elements, but fail to simulate the current of injury, as will be explained later.

The binder may include any biocompatible liquid material that can be mixed with a conductive element (preferably metallic crystals of silver or zinc) to create an ink which may be applied as a thin coating to a surface. One suitable binder is a solvent reducible polymer, such as the polyacrylic non-toxic silk-screen ink manufactured by Colorcon, Inc., a division of Berwind Pharmaceutical Services, Inc. (see Colorcon's No-Tox®product line, part number NT28). The binder is mixed with high purity (at least 99.999%, in an embodiment metallic silver crystals to make the silver ink, in an embodiment. The silver crystals, which are made by grinding silver into a powder, are preferably smaller than 100 microns in size, or about as fine as flour. In an embodiment, the size of the crystals is about 325 mesh, which is typically about 40 microns in size, or a little smaller. The binder is separately mixed with high purity (at least 99.99%, in an embodiment) metallic zinc powder, in an embodiment, which has also preferably been sifted through standard 325 mesh screen, to make the zinc ink. For better quality control and more consistent results, most of the crystals used should be larger than 325 mesh and smaller than 200 mesh. Other powders of metal can be used to make other metallic inks in the same way as just described, in other embodiments.

The ratio of metal to binder affects the release rate of the metal from the mixture. When Colorcon's polyacrylic ink is used as the binder, about 10 to 40 percent of the mixture should be metal for a longer term bandage (one that stays on for about 10 days). If the same binder is used, but the percentage of the mixture that is metal is increased to 60 percent or higher, then the release rate will be much faster and a typical bandage will only be effective for a few days. It should be noted that polyacrylic ink tends to crack if applied as a very thin coat, which exposes more metal crystals which will spontaneously react. For alternate uses, such as on an article of clothing, it may be desired to decrease the percentage of metal down to 5 percent or less, or to use a binder that causes the crystals to be more deeply embedded, so that the primary surface will be antimicrobial for a very long period of time and will not wear prematurely. Other binders may dissolve or otherwise break down faster or slower than a polyacrylic ink, so adjustments should be made to achieve the desired rate of spontaneous reactions from the voltaic cells.

In various embodiments, when a single mass of silver ink is spaced from a single mass of zinc ink, a single voltaic cell is created when an electrolytic solution electrically connects the masses. If a single mass of silver ink is spaced from two masses of zinc ink, then two voltaic cells are created, and so on. To maximize the number of voltaic cells, in various embodiments, a pattern of alternating silver ink masses and zinc ink masses may create an array of electrical currents across the primary surface. A very basic pattern, shown in FIG. 1, has each mass of silver ink equally spaced from four masses of zinc ink, and has each mass of zinc ink equally spaced from four masses of silver ink, according to an embodiment. The first design 6 is separated from the second design 10 by a spacing 8. The designs, which are simply round dots, in an embodiment, are repeated. Numerous repetitions 12 of the designs result in a pattern. For a wound dressing, each silver ink design preferably has about twice as much mass as each zinc ink design, in an embodiment. For the pattern in FIG. 1, the silver ink designs are most preferably about a millimeter from each of the closest four zinc ink designs, and visa-versa. The resulting pattern of dissimilar metal masses defines an array of voltaic cells when introduced to an electrolytic solution.

Figure 2:
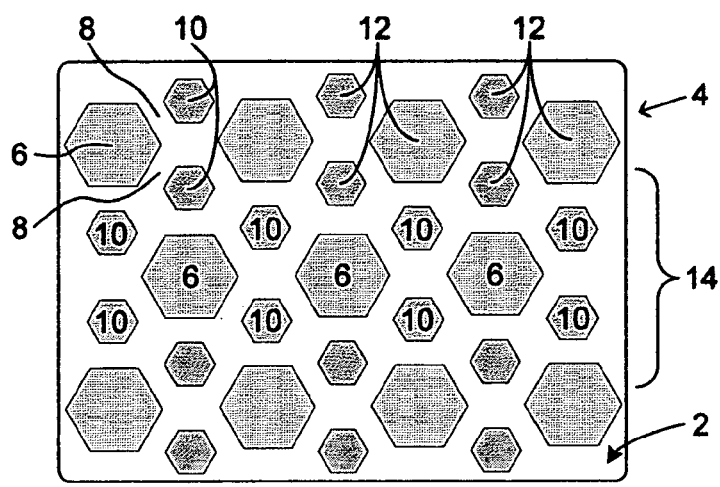
FIG. 2 is a detailed plan view of a pattern of printed electrical conductors in accordance with an embodiment of the present invention.

A dot pattern of ink masses, like the alternating round dots of FIG. 1, is preferred when printing onto a flexible material, such as those used for a wound dressing, because the dots won't significantly affect the flexibility of the material. The pattern of FIG. 1 is well suited for general use. To maximize the density of electrical current over a primary surface, the pattern of FIG. 2 is preferred. The first design 6 in FIG. 2 is a large hexagonally shaped dot, and the second design 10 is a pair of smaller hexagonally shaped dots that are spaced from each other. The spacing 8 that is between the first design and the second design maintains a relatively consistent distance between adjacent sides of the designs. Numerous repetitions 12 of the designs result in a pattern 14 that can be described as at least one of the first design being surrounded by six hexagonally shaped dots of the second design. The pattern of FIG. 2 is well suited for abrasions and burns. There are, of course, other patterns that could be printed to achieve substantially the same results.

Figure 3:
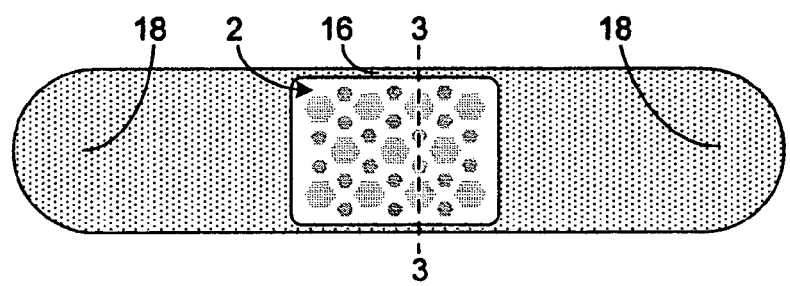
FIG. 3 is an adhesive bandage using the printed pattern of FIG. 2.
Figure 4:
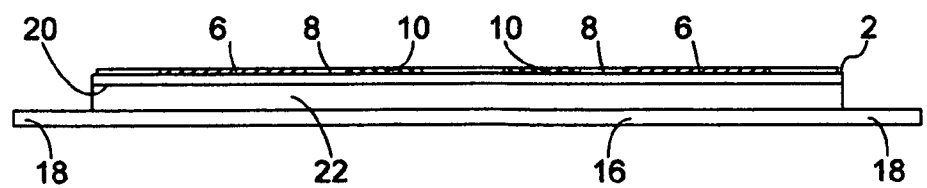
FIG. 4 is a cross-section of FIG. 3 through line 3-3.

FIGS. 3 and 4 show how the pattern of FIG. 2 could be used to make an adhesive bandage. The pattern shown in detail in FIG. 2 is printed onto the primary surface 2 of a wound dressing material. The back 20 of the printed dressing material is fixed to an absorbent cloth layer 22, such as cotton. The absorbent cloth layer is adhesively fixed to an elastic adhesive layer 16 such that there is at least one overlapping piece 18 of the elastic adhesive layer that may be used to secure the wound dressing over a wound.

Figure 5:
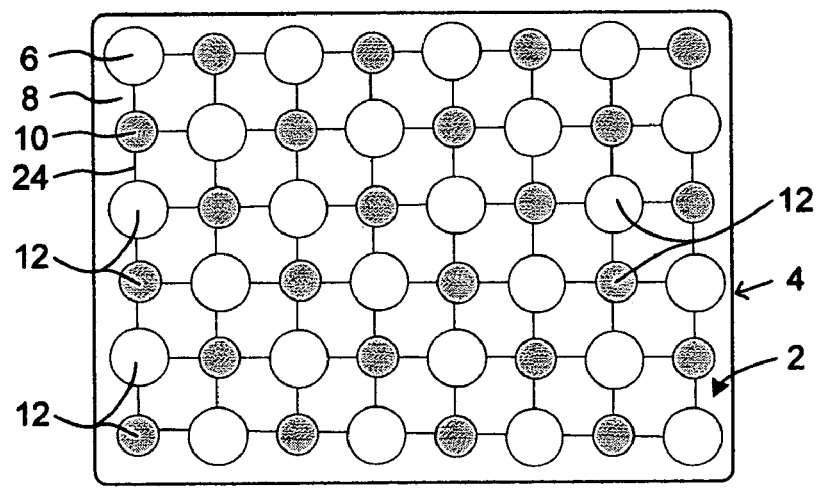
FIG. 5 is a detailed plan view of an alternate embodiment of the present invention which includes fine lines of metal ink connecting electrodes.

FIG. 5 shows an additional feature, which may be added between designs, that will start the flow of current in a poor electrolytic solution. A fine line 24 is printed, using one of the metal inks, along a current path of each voltaic cell. The fine line will initially have a direct reaction, but will be depleted until the distance between the electrodes increases to where maximum voltage is realized. The initial current produced is intended to help control edema so that the wound dressing will be effective. If the electrolytic solution is highly conductive when the wound dressing is initially applied, the fine line will be quickly depleted and the wound dressing will function as though the fine line had never existed.

Figure 6:
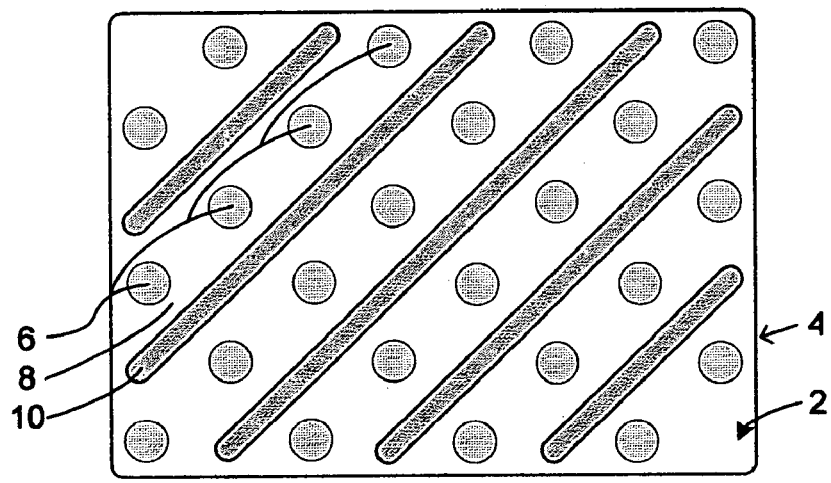
FIG. 6 is a detailed plan view of another alternate embodiment of the present invention having a line pattern and dot pattern.
Figure 7:
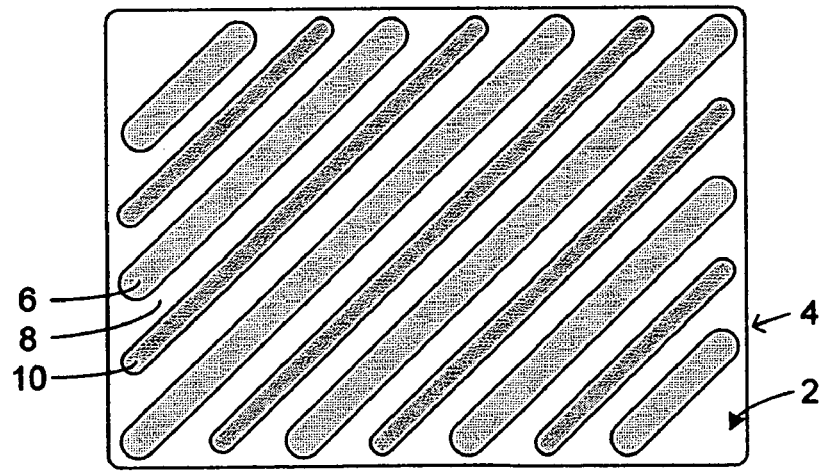
FIG. 7 is a detailed plan view of yet another alternate embodiment of the present invention having two line patterns.

FIGS. 6 and 7 show alternative patterns that use at least one line design. The first design 6 of FIG. 6 is a round dot, similar to the first design used in FIG. 1. The second design 10 of FIG. 6 is a line. When the designs are repeated, they define a pattern of parallel lines that are separated by numerous spaced dots. FIG. 7 uses only line designs. The pattern of FIG. 7 is well suited for cuts, especially when the lines are perpendicular to a cut. The first design 6 may be thicker or wider than the second design 10 if the oxidation-reduction reaction requires more metal from the first conductive element (mixed into the first design's ink) than the second conductive element (mixed into the second design's ink). The lines could be dashed. Another pattern could be silver ink grid lines that have zinc ink masses in the center of each of the cells of the grid. The pattern could even be letters printed from alternating inks so that a message can be printed onto the primary surface-perhaps a brand name.

There are numerous possible creative choices of patterns, but some patterns will work better with certain combinations of inks. Because the spontaneous oxidation-reduction reaction of silver and zinc uses approximately two silver and one zinc, the silver ink design may contain about twice as much mass as the zinc ink design, in an embodiment. At a spacing of about 1 mm between the closest dissimilar metals (closest edge to closest edge), each voltaic cell that is in wound fluid may create approximately 1 volt of potential that will penetrate substantially through the dermis and epidermis. Closer spacing of the dots may decrease the resistance, provide less potential, and the current will not penetrate as deeply. If the spacing falls below about one tenth of a millimeter, a realized benefit of the spontaneous reaction is that which is also present with a direct reaction—silver is electrically driven into the wound, but the current of injury may not be substantially simulated.

The remainder of this description is the second section, which focuses on the basic theories underlying why the present invention promotes wound healing. The introduction of silver metal onto a wound surface and/or into the region of damaged tissue promotes healing by direct suppression of local micro-organisms normally colonizing the wound. Bacterial pathogens commonly include gram-positive cocci such as *Staphylococcus aureus* and group A streptococci and gram-negative bacilli such as *Pseudomonas aeruginosa*, *Escherichia coli*, and *Proteus* spp. The electrochemical nature of silver is such that it is positively charged and thus is able to bind to negatively charged sulfur moieties of the amino acids methionine and cysteine composing critical structural and enzymatic proteins utilized by bacterial cells. The effect of this binding interaction between silver and bacterial proteins is that the proteins' intrinsic chemical bonds are disrupted, causing the bacterial proteins to denature, or change 3-dimensional conformation, and thereby to be functionally ineffective in a way that is of mortal consequence to the bacterial cell.

It has proven to be beneficial to drive silver into the wound. In addition, in accordance with embodiments of the present invention, because the induced electrical current has been shown to electrochemically attract microbes to the surface of the bandage, many of the killed microbes are removed with the bandage instead of accumulating within the wound and necessitating the phagocytic engulfment and removal by macrophages in the natural but slower process of wound healing. Of additional concern in not removing dead bacterial cells from the wound vicinity is the release of toxic enzymes and chemicals from the dead and degrading bacteria, thought to be alleviated by application of embodiments of the present invention. Bacteria and other microbes are specifically drawn to the cathode (silver in the preferred embodiment) by virtue of their overall net negative charge along the created electric gradient. Because all microbes are net negatively charged, they die when they contact silver.

The most preferred material to use in combination with silver to create the voltaic cells of embodiments of the present invention is zinc. Zinc has been well-described for its uses in prevention of infection in such topical antibacterial agents as Bacitracin zinc, a zinc salt of Bacitracin. Zinc is a divalent cation with antibacterial properties of its own in addition to possessing the added benefit of being a cofactor to proteins of the metalloproteinase family of enzymes important to the phagocytic debridement and remodeling phases of wound healing. As a cofactor, zinc promotes and accelerates the functional activity of these enzymes, resulting in better, more efficient wound healing.

In a wound, the absence of the positively charged epithelium-negatively charged dermis combination which is normally observed in healthy tissue results in a deficit in the naturally occurring potential difference across the body surface. The silver-zinc voltaic cells of the preferred embodiment of the present invention recreates the physiologic current of injury important to the induction of neutrophil, macrophage and fibroblast cells essential to the healing process. In addition, the simulated current of injury stimulates regional nerve endings to promote their involvement in wound resolution.

The voltage present at the sight of a wound has been traditionally in the range of millivolts, but embodiments of the present invention may introduce a much higher voltage, near 1 volt when using the 1 mm spacing of dissimilar metals already described. The higher voltage is believed to drive the current deeper into the wound bed so that dermis and epidermis benefit from the simulated current of injury. In this way, the current not only drives some silver and zinc into the wound to kill microbes, but the current also provides the stimulatory current of injury so that the entire wound surface area can heal simultaneously, in an embodiment. Without the wound dressing of embodiments of the present invention, the current of injury may only naturally exist at the periphery of the wound that is within about half a millimeter of undamaged skin. That is why a wound closes from the edges in. A benefit of covering the entire wound with a simulated current of injury, in accordance with various embodiments, is that the volume of skin being repaired at the same time may be significantly increased.

A further benefit of a current producing wound dressing addresses the medically known fact that a wound closes faster if it is kept moist and clean. Edema should be minimized without allowing the wound surface to desiccate. The moisture balance of a wound should allow the damaged area to remain electrically conductive so that there are not areas of high resistance that block conduction of the simulated current of injury from penetrating into the tissue. Any excessive moisture and swelling creates an ideal environment for the growth of bacteria and microbes. Excess moisture that causes the damaged tissue to swell is best drawn out of the wound by being absorbed into cotton or another absorbent cloth material that will wick the excess moisture off the top of the wound surface without promoting any drying of the damaged tissue.

Finally, it is preferable to control the release rate of the dissimilar metals of the current producing wound dressing of various embodiments for two reasons, each in opposition to the other. In the preferred embodiment, the voltaic cells of the wound dressing drive the simulated current of injury deeper into the wound area if the dissimilar metals are kept separated by a predetermined distance, such that it would be undesirable to allow the silver to freely mix into the wound fluids as this would quickly result in a quenching of the electrochemical gradient and thus an extinguishing of the desired voltaic effect. On the other hand, if a predetermined quantity of silver is allowed to mix into the wound, the silver will help prevent wound infection. (Please note that the spontaneous reactions of the voltaic cells will release elements into the wound even though the most desired method of killing microbes is at the cathodes, as already described.)

Because it is desirable to have both the current of injury and the antimicrobial effects of silver present, a compromise may be made. To achieve a balance, the binder should release silver and zinc into the wound while simultaneously maintaining the simulated current of injury for the entire period of time that the bandage is intended to be left on the wound. Wound dressings that should be changed more often can have a shorter life as a current producing dressing, so the release rate of the binder can be faster. Wound dressings that are intended to be left on the wound for an extended period of time, say 10 days, should have a binder that does not dissolve or otherwise breakdown as quickly, or the percentage of binder to metallic crystals should be higher. This can be controlled by the intelligent selection of different mixture ratios and/or binder materials having longer or shorter half-lives or absorption rates, in various embodiments.

While various embodiments of the invention have been shown and described, it will be realized that alterations and modifications may be made thereto without departing from the scope of the following claims. For example, it may be desirable to use methods other than a common screen printing machine to print the electrodes of the present invention onto surfaces on medical instruments, garments, implants and the like so that they are antimicrobial. It is expected that other methods of applying the paint or ink may be substituted as appropriate. Also, there are numerous shapes, sizes and patterns of voltaic cells that have not been described, but it is expected that this teaching will enable those skilled in the art to incorporate their own designs which will then be painted or printed onto a surface to create voltaic cells which will become active when brought into contact with an electrolytic solution.

What is claimed is:

1. A wound dressing comprising:

a primary surface of a pliable dressing material, wherein the pliable dressing material is adapted to be applied to an area of damaged tissue;

a first design formed from a first ink that includes a mixture of a polymer and a first element, the first ink being printed into a position of contact with the primary surface, the first element including a metal species, and the first design including at least one dot, wherein selective ones of the at least one dot have approximately a 1.5 mm+/− 1 mm mean diameter;

a second design formed from a second ink that includes a mixture of a polymer and a second element, the second element including a different metal species than the first element, the second ink being printed into a position of contact with the primary surface, and the second design including at least one other dot, wherein selective ones of the at least one other dot have approximately a 2.5 mm+− 2 mm mean diameter;

a spacing on the primary surface that is between the first design and the second design such that the first design does not physically contact the second design, wherein the spacing is approximately 1.5 mm+− 1 mm; and at least one repetition of the first design and the second design, the at least one repetition of the first design being substantially adjacent the second design, wherein the at least one repetition of the first design and the second design, in conjunction with the spacing between the first design and the second design, defines at least one pattern of at least one voltaic cell for spontaneously generating at least one electrical current when introduced to an electrolytic solution.

2. A wound dressing comprising:

a primary surface of a pliable dressing material, wherein the pliable dressing material is adapted to be applied to an area of damaged tissue;

a first design formed from a first ink that includes a mixture of a polymer and a first element, the first ink being printed into a position of contact with the primary surface, the first element including a metal species, and the first design including at least one hexagonally shaped dot;

a second design formed from a second ink that includes a mixture of a polymer and a second element, the second element including a different metal species than the first element, the second ink being printed into a position of contact with the primary surface, and the second design including at least one other dot, the at least one other dot including two hexagonally shaped dots that are spaced from each other;

a spacing on the primary surface that is between the first design and the second design such that the first design does not physically contact the second design; and at least one repetition of the first design and the second design, the at least one repetition of the first design being substantially adjacent the second design wherein multiple repetitions of the first design and the second design result in at least one pattern characterized by the first design being surrounded by six hexagonally shaped dots of the second design, wherein the at least one pattern defines at least one voltaic cell for spontaneously generating at least one electrical current when introduced to an electrolytic solution.

3. A method of making a wound dressing comprising:

applying a first fluid to a face of a pliable dressing material to form a first design, wherein the first fluid includes a first biocompatible polymer and a first element;

applying a second fluid to the face of the pliable dressing material to form a second design such that the second design is not physically contacting the first design, wherein the second fluid includes a second biocompatible polymer and a second element;

repeating the first design and the second design to create a pattern that alternates between the first design and the second design;

fixing an absorbent cloth layer to a back of the pliable dressing material, wherein the back of the pliable dressing material comprises a surface opposite the face of the pliable dressing material; and bonding an elastic adhesive layer to the absorbent cloth layer such that there is at least one overlapping piece of the elastic adhesive layer for securing the face of the pliable dressing material over an area of damaged tissue in a manner that allows the first and second elements of the corresponding first and second fluids to be introduced directly to the area of damaged tissue.

4. The method of claim 3 wherein the first element includes a silver powder, and wherein the second element includes a zinc powder.

5. The method of claim 4 wherein applying the first fluid and applying the second fluid include screen printing the first fluid and the second fluid onto the face of pliable dressing material.

6. The method of claim 4 wherein at least some of the particles of the silver powder are approximately 100 microns or less in size.

7. The method of claim 3 wherein:

the first design includes at least one dot, and selective ones of the at least one dot have an approximately 1.5 mm± 1 mm mean diameter;

a second design includes at least one other dot, and selective ones of the at least one other dot have an approximately 2.5 mm± 2 mm mean diameter; and forming a spacing on the pliable dressing material between the at least one dot of the first design and the at least one other dot of the second design such that the first design does not physically contact the second design, the spacing being approximately 1.5 mm± 1 mm.

* * * * *